(12) United States Patent
Niemann et al.

(10) Patent No.: US 9,470,622 B2
(45) Date of Patent: Oct. 18, 2016

(54) SENSOR DEVICE HAVING OPTICS INCLUDING DECOUPLING AND COUPLING REGIONS

(71) Applicant: Hella KGaA Hueck & Co., Lippstadt (DE)

(72) Inventors: Thomas Niemann, Delmenhorst (DE); Carsten Thun, Bremen (DE)

(73) Assignee: HELLA KGAA HUECK & CO., Lippstadt (DE)

( * ) Notice: Subject to any disclaimer, the term of this patent is extended or adjusted under 35 U.S.C. 154(b) by 82 days.

(21) Appl. No.: 14/292,074

(22) Filed: May 30, 2014

(65) Prior Publication Data

US 2014/0353474 A1 Dec. 4, 2014

(30) Foreign Application Priority Data

May 30, 2013 (DE) .................. 10 2013 009 126

(51) Int. Cl.

| G01N 21/00 | (2006.01) |
|---|---|
| G01N 21/17 | (2006.01) |
| G01J 1/02 | (2006.01) |
| G01N 21/55 | (2014.01) |
| B60S 1/08 | (2006.01) |

(52) U.S. Cl.
CPC ............. *G01N 21/17* (2013.01); *B60S 1/0837* (2013.01); *G01J 1/02* (2013.01); *G01N 21/55* (2013.01); *B60S 1/0888* (2013.01)

(58) Field of Classification Search
CPC .... G01N 21/17; G01N 21/55; B60S 1/0837; G01J 21/17; G01J 1/02
See application file for complete search history.

(56) References Cited

FOREIGN PATENT DOCUMENTS

| DE | 4006174 | A | 7/1991 | |
|---|---|---|---|---|
| DE | 10001705 | A | 7/2001 | |
| DE | 19830120 | B4 | 7/2006 | |
| DE | 102007036492 | | 2/2009 | |
| DE | 102007039349 | | 2/2009 | |
| DE | 102008061616 | | 6/2010 | |
| FR | 2722291 | A1 * | 12/1996 | ............. G01N 21/41 |

* cited by examiner

*Primary Examiner* — Tony Ko

(74) *Attorney, Agent, or Firm* — Muncy, Geissler, Olds & Lowe, P.C.

(57) ABSTRACT

A sensor device for detecting moisture on a windscreen has a transmitter and a receiver and optics arranged between the transmitter and the receiver. The optics have an upper plane for connection to a windscreen, a decoupling region serving to decouple the electromagnetic rays from the optics into the windscreen, and a coupling region serving to couple the electromagnetic radiation from the windscreen into the optics, and which even for a small construction shall supply a usable signal. The decoupling region has at least one surface inclined relative to the upper plane of the optics.

12 Claims, 3 Drawing Sheets

SENSOR DEVICE HAVING OPTICS INCLUDING DECOUPLING AND COUPLING REGIONS

BACKGROUND OF THE INVENTION

1. Field of the Invention

The invention relates to a sensor device for detecting moisture on a windscreen comprising a transmitter and a receiver and optics arranged between the transmitter and the receiver, wherein the optics comprises an upper plane for connection to a windscreen, and wherein the optics comprises a decoupling region serving to decouple the electromagnetic rays from the optics into the windscreen, and a coupling region serving to couple the electromagnetic radiation from the windscreen into the optics. Furthermore the invention relates to optics for a sensor device of this kind and a motor vehicle with a windscreen and a sensor device arranged thereon.

2. Brief Discussion of the Related Art

The DE 40 06 174 C1 has disclosed a sensor device of the kind mentioned in the beginning. The windscreen has an optics arranged on it, which at one end has radiation introduced into it from a radiation transmitter. The radiation is reflected multiple times in the optics and in the plane supported against the topside of the optics. Decoupling of the rays from the windscreen depends upon the degree of wetting of the windscreen. The other end of the optics has a receiver arranged on it, which supplies a signal inversely proportional to the amount of precipitation. The sensor device operates according to the optical principle of total reflection.

The basic problem consists in that the space available for the sensor device is becoming increasing smaller. This means that the surface of the optics forming the sensing region, is also reduced in size. As a result a signal of diminished accuracy is obtained.

SUMMARY OF THE INVENTION

The invention is therefore based on the requirement to provide a sensor device of the kind mentioned in the beginning, which even for a small-size construction continues to supply a usable signal for detecting moisture on a windscreen.

The solution to this requirement is a sensor device with the characteristics of patent claim 1. As regards an optics the solution is supplied by the characteristics of patent claim 11 and as regards a motor vehicle the solution is supplied by the characteristics of patent claim 12.

A sensor device for detecting moisture on a windscreen with a transmitter and a receiver and an optics arranged between the transmitter and the receiver, the optics comprising an upper plane for connection to a windscreen and a decoupling region serving to decouple the electromagnetic rays from the optics into the windscreen and a coupling region serving to couple the electromagnetic radiation from the windscreen into the optics, is characterised in that according to the invention the decoupling region comprises at least one surface inclined relative to the upper plane of the optics, and in that the inclined surface comprises an angle of inclination between 2° and 20° relative to the upper plane. As a result the electromagnetic rays introduced by the transmitter into the optics are coupled particularly well into the windscreen. The upper plane of the optics is not a continuous plane in terms of a surface, but denotes the entire area adjoining the windscreen. This area is not continuously planar, but for example comprises, according to the invention, the inclined surfaces in the decoupling region.

Preferably the inclined surface comprises an angle of inclination between 4° and 10° relative to the upper plane, in particular it comprises an angle of inclination between 4° and 7° relative to the upper plane. Especially preferred is an inclined surface of 5° relative to the upper plane. Preferably the inclined surface of the decoupling region is inclined in direction of the coupling region. Since the receiver transmits the electromagnetic radiation laterally into the optics, the angle at which the electromagnetic rays hit the inclined surface is larger relative to a non-inclined surface. Preferably the decoupling region comprises several inclined surfaces. In an especially preferred embodiment the decoupling region comprises four inclined surfaces. Of these four inclined surfaces at least two are inclined in direction of the coupling region. Preferably, however, one inclined surface, or two of the inclined surfaces in another embodiment, are inclined in direction of the transmitter.

In another preferred embodiment of the invention the coupling region again comprises at least one surface inclined relative to the upper plane of the optics. The coupling region is the region, in which the light is coupled from the windscreen into the optics. This is arranged adjacent to the receiver of the sensor device. Due to this configuration of the geometry of the coupling region, an especially good decoupling of the light from the windscreen into the coupling region is achieved. The inclined surface of the coupling region preferably comprises an angle of inclination between 2° and 20° relative to the upper plane of the optics and especially preferably an angle of inclination between 4° and 10° relative to the upper plane of the optics. Especially preferably the inclined surface is at an angle of 5° relative to the upper plane of the optics. In a preferred design the coupling region comprises at least two inclined surfaces the inclined surfaces of which are aligned with each other in opposite directions, in particular such that they are inclined towards each other. In an alternative preferred embodiment the coupling region comprises two or more inclined surfaces which in their inclination extend in direction of the decoupling region. It is preferred if these are formed on the edge, i.e. particularly close to the receiver. The inclined surface most remote from the receiver or the inclined surfaces most remote and second most remote from the receiver are preferably inclined in direction of the receiver, i.e. inclined in opposite direction to the previously mentioned inclined surfaces.

In another further development of the invention the optics comprises a convex shape between the decoupling region and the coupling region on its underside, i.e. opposite the upper plane. This especially adapted geometric shape on the underside of the optics ensures that inner total reflection is achieved thereby ensuring that the electromagnetic rays are reflected inside the optics virtually without any losses. This convex shape is arranged between the coupling region and the decoupling region. The inclined surfaces of the decoupling region are inclined in direction of the coupling region. Only the inclined surfaces which are completely above the intermediate region of the underside which comprises the convex shape, are inclined with their inclination in direction of the coupling region. The same applies vice versa to the inclined surfaces of the coupling region. Only the inclined surfaces in the coupling region which are completely above the intermediate region with the convex shape on the underside, are inclined in direction of the coupling region/the receiver.

In another further development of the invention the optics, on its topside, comprises a central planar region between the decoupling region and the coupling region. This region ultimately separates the coupling region and the decoupling region from each other. On the underside there is the intermediate region which overlaps the respectively central portions of the coupling region and the decoupling region. According to another preferred further development of the invention the optics comprises a coupling optics opposite the transmitter, which is configured like a bowl with a convex outwardly protruding floor. This results in particularly good focussing and the collection of scattered light. This means that a maximum coupling of light into the optics is achieved. It is preferred if the sensor device including the transmitter and the receiver preferably configured as diodes, is tuned to wavelengths between 880 nm and 920 nm.

Another aspect of the invention relates to the provision of an optics for the above mentioned sensor device, wherein the optics comprises an upper plane for connection to a windscreen and wherein the optics comprises a decoupling region serving to decouple the electromagnetic rays from the optics into the windscreen and a coupling region serving to couple the electromagnetic radiation from the windscreen into the optics. Furthermore the optics, in its decoupling region, comprises, according to the invention, at least one surface inclined relative to the upper plane of the optics.

A further aspect of the invention consists in providing a motor vehicle with a windscreen and a sensor device arranged thereon for detecting moisture on a windscreen. The sensor device is configured corresponding to the above description.

BRIEF DESCRIPTION OF THE DRAWINGS

The invention will now be explained in detail with reference to an embodiment shown in the drawing, which comprises three schematic illustrations, as follows.

DETAILED DESCRIPTION OF THE PREFERRED EMBODIMENTS

Figure 1:
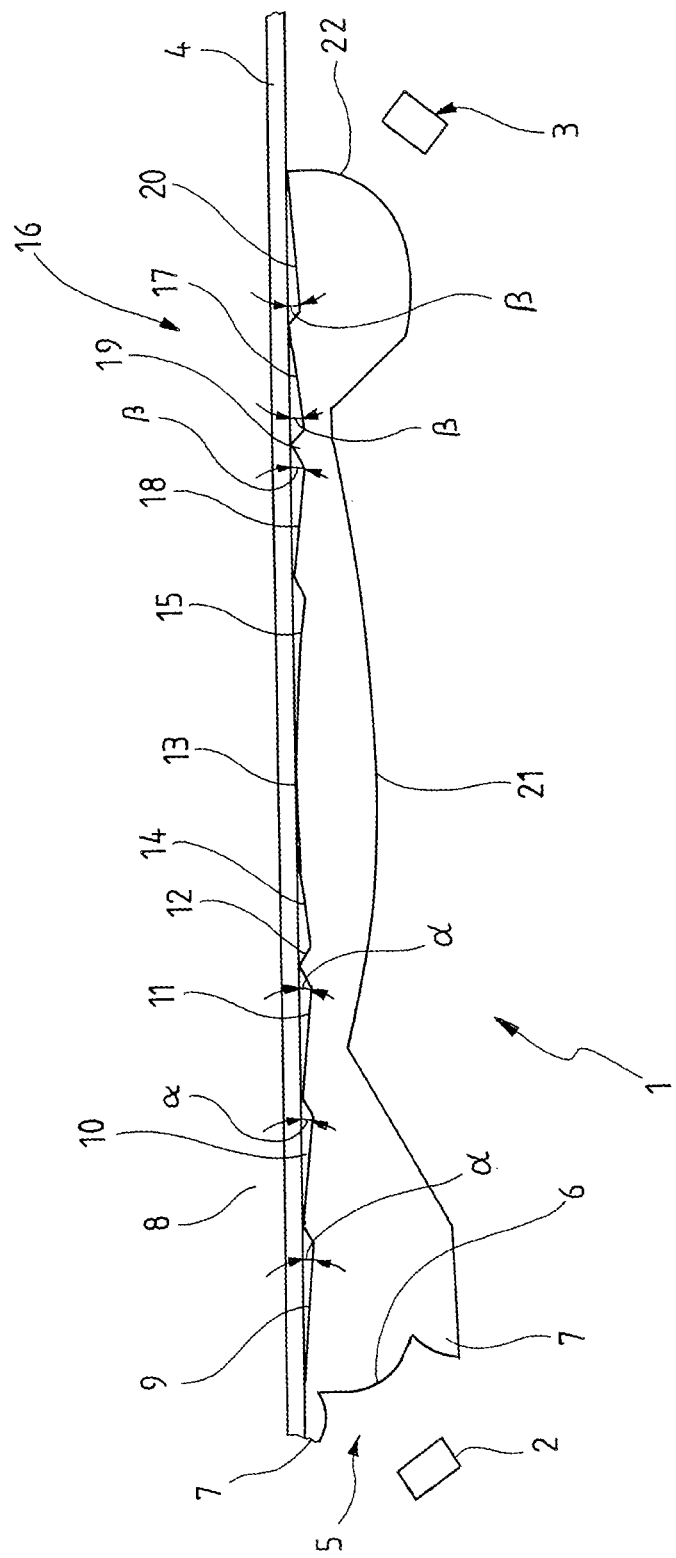
FIG. 1 shows a cross-section of a sensor device according to the invention, schematically drawn with a windscreen arranged thereon.

FIG. 1 shows a cross-section through the sensor device according to the invention in a housing with a windscreen 4 arranged thereon. Essentially the sensor device comprises an optics 1, a transmitter 2 and a receiver 3. The optics is arranged supported against a windscreen 4. The optics comprises an upper plane 13 for connection to the windscreen. The optics 1 does not comprise a continuous upper plane, but is shaped only partially in the upper area in a planar manner. The term upper plane denotes the topside, which is provided for connection to the windscreen 4. The transmitter 2 is typically configured as a diode and radiates electromagnetic rays into the optics 1. To this end the optics 1 comprises a coupling optics 5 opposite the transmitter 2, which is configured in the shape of a bowl 7 with a convex outwardly protruding floor 6. From the optics 1 the electromagnetic rays then reach the windscreen 4 via a decoupling region 8. The electromagnetic rays are reflected from the topside of the windscreen 4 and are ultimately reflected several times between the optics 1/its underside 21 and the topside of the windscreen 4. When the windscreen 4 is wetted with water or rain, electromagnetic rays are decoupled from this system and the intensity decreases. The decrease in intensity at the receiver 3 which typically is also a diode, then is a measure for the wetting of the windscreen 4 on the topside. The decoupling region 8 in the embodiment shown comprises three inclined surfaces 9, 10 and 11, which have an inclination in direction of the receiver 3 or a coupling region 16 arranged in the vicinity of the receiver 3. The angle $\alpha$ is between 2° and 20°, preferably between 4° and 10° and in particular between 5° and 8°. Due to this geometry on the topside of the light conductor a particularly good coupling of the light from the optics 1 and a particularly good coupling of the light into the windscreen 4 is achieved. Furthermore a surface 14 is provided which lies mirror-symmetrically opposite one of the inclined surfaces 11, which is inclined in the opposite direction, i.e. in direction of the receiver of the transmitter 2. The inclined surfaces 11 and 14 are separated from each other by a point 12 triangular in cross-section. The surface 14 inclined towards the transmitter 2 lies completely above the underside 21 insofar as this has a convex shape and lies between the decoupling region 16 and the coupling region 8. Approximately in the middle of the optics 1 a central planar region 13 is provided. This is indeed planar and configured so as to be supported against the windscreen. In the right-hand area of FIG. 1, i.e. adjacent to the receiver 3 a coupling region 16 is provided, in which a maximum of electromagnetic rays from the windscreen 4 is coupled into the optics 1/decoupled from the windscreen 4. Here again several inclined surfaces are provided. These are in particular the surfaces 17 and 20, which are directly adjacent to the receiver 3 and are inclined in direction of the transmitter 2 or in direction of the decoupling region 8. The surfaces 17 and 20 are inclined at an angle $\beta$ relative to the upper plane 13. The angle of inclination is between 2° and 20°, in particular between 4° and 10° and especially preferred between 5° and 8°. In a direction adjoining the transmitter 2 a further inclined surface 18 is provided which is inclined in direction of the receiver 3. The surfaces 18 and 17 are arranged symmetrically to each other to the right and left of a structure 19 triangular in cross-section. The surface 18 is completely above the convex underside 21 of the optics 1. In direction of the transmitter 2 next to it there is a further inclined surface 15 which is also inclined in direction of the receiver 3, i.e. comprises the same inclination as the inclined surface 18. The surfaces 15, 17, 18 and 20 are all inclined at the same angle, in particular at an angle between 4° and 8°. The surfaces 15 and 18 have an inclination in direction of the receiver 3, whilst the surfaces 17 and 20 have an inclination in direction of the transmitter 2. These two groups of surfaces are therefore inclined in opposite directions towards each other.

Figure 2:
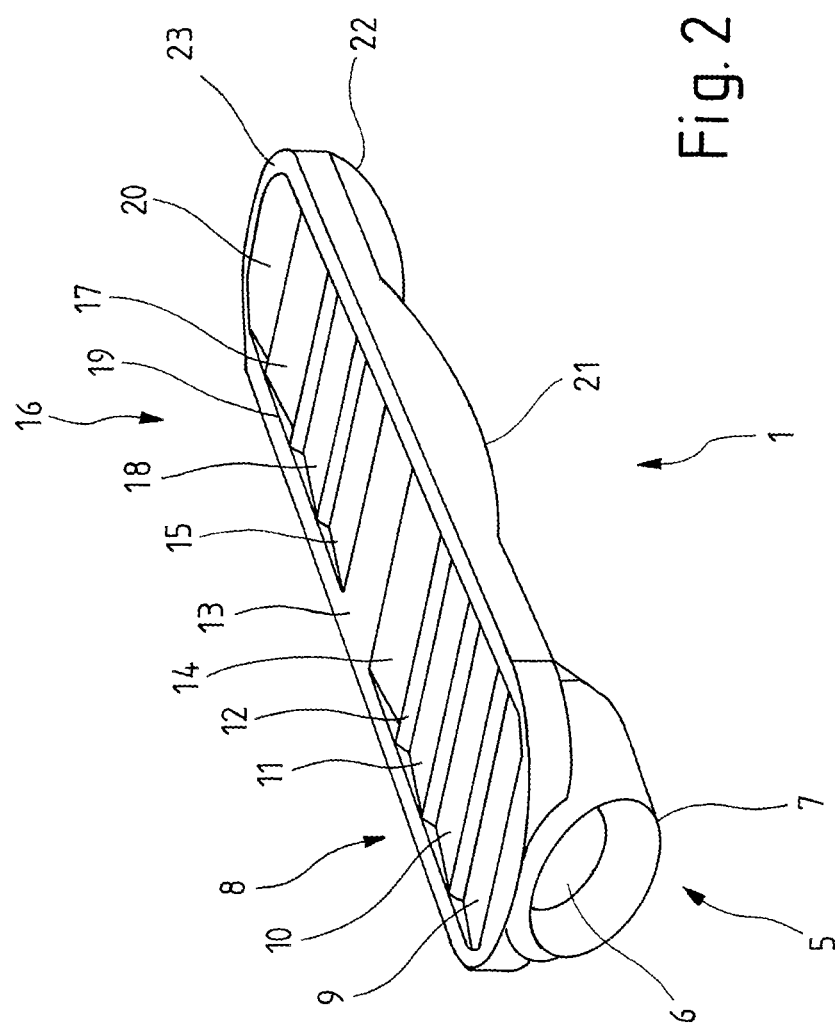
FIG. 2 shows a perspective view of the optics of the sensor device of FIG. 1.

FIG. 2 shows an optics 1 in a perspective view. In contrast to FIG. 1 neither the windscreen 4 nor the transmitter 2 nor the receiver 3 are shown. What is clearly visible is the coupling optics 5 which is shaped in form of a bowl 7 and which comprises a floor 6 protruding convexly outwardly in direction of transmitter 2. The upper plane provided for contacting the windscreen 4, is formed in a central region 13 and is configured as a plane in a circumferential frame 23. In the remaining regions provision is made essentially for the inclined surfaces 9, 10, 11 and 14 of the decoupling region 8 and the inclined surfaces 15, 17, 18 and 20 of the coupling region 16. A decoupling optics 22 is provided adjacently to the receiver 3. This is configured essentially as a convexly shaped spherical surface.

Figure 3:
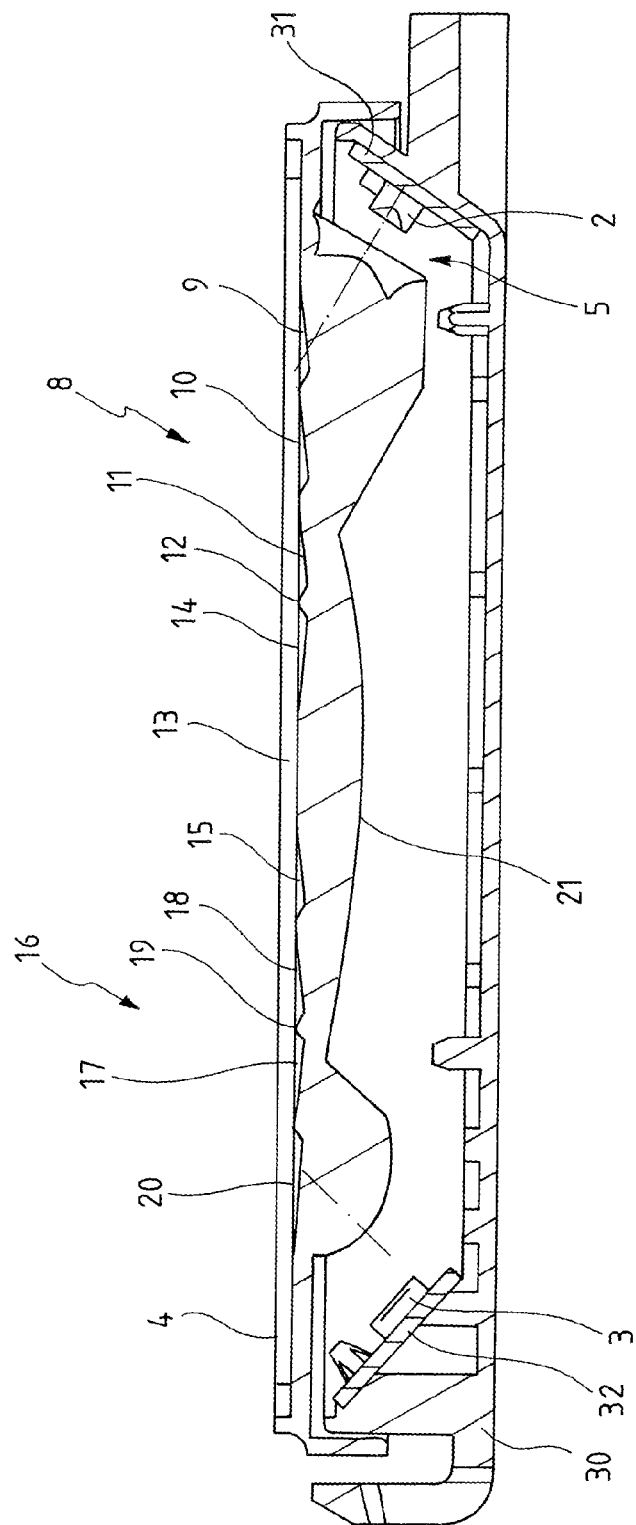
FIG. 3 shows a cross-section through the sensor device according to the invention in a housing.

FIG. 3, in comparison to FIG. 1, shows the device according to the invention in cross-section. In contrast to FIG. 1 this shows the device laterally reversed, i.e. the transmitter 2 is arranged on the right-hand side and the receiver 3 is arranged on the left. Identical parts are marked with the same reference symbols. A housing 30 is provided, in which the transmitter 2 is arranged on a printed circuit board 31 and in which the receiver 3 is arranged on a printed circuit board 32. Transmitter and receiver are preferably diodes, which operate in the infrared range between 880 nm and 920 nm.

On the inclined surfaces the angles are shown. These are 5° for the incline and 47° for the short inclined surface. The convexly shaped underside 21 is configured as part of the circumference of a circle.

All features mentioned in the above description and the claims can be combined at random with any of the features of the independent claim. The disclosure of the invention is therefore not limited to the described/claimed feature combinations, rather all feature combinations which are meaningful in terms of the invention are to be considered as disclosed.

The invention claimed is:

1. A sensor device for detecting moisture on a windscreen comprising a transmitter and a receiver and optics arranged between the transmitter and the receiver, wherein the optics comprises an upper plane for connection to a windscreen and wherein the optics comprises a decoupling region serving to decouple the electromagnetic rays from the optics into the windscreen, and a coupling region serving to couple the electromagnetic radiation from the windscreen into the optics,
wherein
  the decoupling region comprises at least two surfaces inclined relative to the upper plane of the optics,
  the at least two surfaces are inclined in direction of the coupling region, and
  each of the at least two inclined surfaces comprises an angle of inclination between 2° and 20° relative to the upper plane.

2. The sensor according to claim 1, wherein the inclined surface comprises an angle of inclination between 4° and 10° relative to the upper plane.

3. The sensor according to claim 1, wherein the coupling region comprises at least one inclined surface relative to the upper plane of the optics.

4. The sensor according to claim 3, wherein the inclined surface of the coupling region comprises an angle of inclination between 2° and 20° relative to the upper plane of the optics.

5. The sensor according to claim 4, wherein the inclined surface of the coupling region comprises an angle of inclination between 4° and 10° relative to the upper plane of the optics.

6. The sensor according to claim 3, wherein the coupling region comprises at least two inclined surfaces, the inclined surfaces of which are aligned with each other in opposite directions, in particular are aligned in their inclination towards each other.

7. The sensor according to claim 1, wherein the optics between the decoupling region and the coupling region comprises a convex shape on its underside, i.e. opposite the upper plane.

8. The sensor according to claim 1, wherein the optics on its topside between decoupling region and coupling region comprises a central planar region.

9. The sensor according to claim 1, wherein the optics comprises a coupling optics opposite the transmitter, which is configured like a bowl with a convex outwardly protruding floor.

10. A motor vehicle with a screen and a sensor assembly arranged thereon according to claim 1.

11. The motor vehicle with a screen according to claim 10, wherein the screen is a windscreen.

12. Optics for a sensor device, with an upper plane for connection to a windscreen and a decoupling region serving to decouple the electromagnetic rays from the optics into the windscreen, and a coupling region serving to couple the electromagnetic radiation from the windscreen into the optics,
wherein
  the decoupling region comprises at least two surfaces inclined relative to the upper plane of the optics,
  the at leas two surfaces are inclined in direction of the coupling region, and
  each of the at least two inclined surfaces comprises an angle of inclination between 2° and 20° relative to the upper plane.

* * * * *